United States Patent [19]

Motoyama et al.

[11] Patent Number: 4,794,934
[45] Date of Patent: Jan. 3, 1989

[54] APPARATUS FOR DIAGNOSING THE FUNCTIONS OF THE INTERNAL ORGANS AND AUTONOMIC NERVOUS SYSTEM OF THE LIVING BODY

[76] Inventors: Hiroshi Motoyama, 11-1, Inogashira 4-chome, Mitaka-shi, Tokyo, 181, Japan; Fumiaki Nukada, 9-7, Yahatacho 4-chome, Musashino-shi, Tokyo, 180, Japan

[21] Appl. No.: 32,517
[22] PCT Filed: Mar. 10, 1986
[86] PCT No.: PCT/JP86/00122
  § 371 Date: Feb. 24, 1987
  § 102(e) Date: Feb. 24, 1987
[87] PCT Pub. No.: WO87/00024
  PCT Pub. Date: Jan. 15, 1987

[30] Foreign Application Priority Data

Jun. 27, 1985 [JP] Japan ............................ 60-138899

[51] Int. Cl.⁴ ............................................... A61B 5/05
[52] U.S. Cl. .................................. 128/734; 364/417; 364/413.02
[58] Field of Search ............... 128/734, 735; 364/415, 364/417

[56] References Cited

U.S. PATENT DOCUMENTS 3,971,366  7/1976  Motoyama .
4,486,835  12/1984  Bai et al. .

FOREIGN PATENT DOCUMENTS 52-5643   1/1977  Japan .
52-97277  8/1977  Japan .
54-149290 11/1979 Japan .
59-82006  6/1984  Japan .
197709    9/1977  U.S.S.R. ............................ 128/734

OTHER PUBLICATIONS

S. Grimmes, "Impedance Measurement of Individual Skin Surface Electrodes" Nov. 1983, Medical & Bio. Engr. & Computing, pp. 750-755.
A. Van Boxtel "Skin Resistance During Square-Wave Electrical Pulses of 1 to 10 mA", Nov., 1977, Medical & Bio. Engr. & Computing, pp. 679-687.

Primary Examiner—William E. Wayner
Attorney, Agent, or Firm—McGlew and Tuttle

[57] ABSTRACT

An apparatus for diagnosing the functions of the internal organs and the autonomic nervous system of the living body in which a constant voltage is applied across two or more electrodes attached to the living body, a current flowing across the electrodes and changing from time to time is detected at high speed and recorded, and predetermined parameters are calculated from the recorded data is disclosed. The electrodes are sequentially or arbitrarily scanned by an electrode scanning means (2), and the constant voltage generated by a constant voltage generating means (3) is applied to the scanned electrodes. The instantaneous value of the current flowing across two electrodes is detected by a detecting means (4), and recorded as a digital value in a recording means (5). The data recorded in the recording means (5) are displayed on a display means (7) via a transmitting means (8), and/or the parameters calculated by a calculating means (6) from the data recorded in the recording means (5) are displayed on the display means (7).

10 Claims, 11 Drawing Sheets

APPARATUS FOR DIAGNOSING THE FUNCTIONS OF THE INTERNAL ORGANS AND AUTONOMIC NERVOUS SYSTEM OF THE LIVING BODY

DESCRIPTION

1. Technical Field

This invention relates to an apparatus for diagnosing the functional condition of the internal organs of the living body and the balance condition of the autonomic nervous system thereof.

2. Background Art

In general, Western medicine relies mainly on the methods of biochemical clinical examination for inspection and diagnosis of the functions of internal organs and the diseases thereof, except for electrocardiograms for measuring the functions of the heart. These biochemical examinations, however, involve a lot of money, time and labor, and are often associated with pains on the part of the patients who undergo the examinations.

On the contrary, it has been well-known that Oriental medicine, especially acupuncture and moxa cautery medicine, achnowledges, through its clinical experiences, the existence of the systems called "Keiraku" (which can be regarded as the stimulation receptor or reactor systems) throughout the whole living body, identifies a close relationship of these "Keiraku" systems with certain internal organs and with the autonomic nerves that control these organs. Based on such knowledge, it detects the abnormal condition of a reaction point (this point is often referred to as the "Keiketsu" point, or more popularly "Tsubo") in the "Keiraku" system to diagnose the existence of disease in each internal organ, which is related to the corresponding reaction point, or brings the abnormal condition to normal by giving physical stimulation, such as needle puncturing, application of heat or electric stimuli, etc., to the reaction point which is in the abnormal condition.

In order to pinpoint a reaction point that is in an abnormal condition among numerous reaction, it has been a general practice to rely on the feel of the fingertips of the diagnostician and the tactile reaction by the patient. This, however, requires years of experience and a high degree of skill on the part of the diagnostician. Thus, there have been devised various types of apparatus which can perform electrical detection and diagnosis of the condition of the reaction points by taking advantage of the fact that electric resistance, or impedance, falls off greatly at the reaction points ("Keiketsu" points) in the skin, without recourse to the experience and skill of the diagnostician. A "Skin Ammeter" or "Neurometer" is one example of such apparatus. In using this type of apparatus, a roller electrode is moved around various parts of the body, such as the trunk, hands, feet, etc. while holding the electrode in contact with the skin surface, with another stationary electrode attached to the skin surface of a given part of the body to detect electric resistance or impedance appearing across the electrodes. The change in electric resistance or impedance at every checking point is observed to diagnose the functional condition of the internal organs and the existence of illness and, in some cases, to perform medical treatment. The use of a skin ammeter, however, has a number of shortcomings as follows.

(a) Since the trunk of the body has a great number of reaction points (as many as 300 points, for instance) with respect to a Keiraku system corresponding to one internal organ, it takes a lot of time to examine the points.

(b) Varied size and depth from the skin surface of the reaction points often make it difficult to locate a particular reaction point to be inspected.

(c) As the voltage applied to the skin surface is relatively high, i.e., 9-27V, an examination process by repeatedly bringing the roller electrode into contact with the skin surface would cause electrical reactions on the skin surface, leading to excitation reactions everywhere on the body surface. This makes it impossible to obtain accurate measurements.

As another means for detecting abnormality at the reaction points, a heat sensitivity meter is known. Taking advantage of the fact that the "Keiketsu" points, or the reaction points at the tips of fingers and toes serve as terminal points (often referred to as the "Seiketsu" points) of all "Keiraku" systems, the heat sensitivity meter gives a constant heat stimulatin continuously to the "Seiketsu" points, or the terminal points of all "Keiraku" systems until the patient begins to feel the heat. The threshold at which the patient feels the heat at each "Seiketsu" point is expressed in a numerical value. Based on the difference in numerical values representing thresholds at various "Seiketsu" points, an extremely abnormal "Keiraku" system can be located. Although this heat sensitivity meter is helpful in knowing the change in heat sensitivity around "Keiketsu" points and examining heat sensory nerves, the heat used for measurement tends to stimulate the fingers and toes, causing the temperature of the fingers and toes to rise or changing the sensitivity of the measured part. This makes it difficult to obtain accurate numerical values. In addition, this method sometimes gives considerable pain to the patient.

As an apparatus which solves the aforementioned problems, the following apparatus for diagnosing the functions of the internal organs and the automatic nervous system has been invented (Japanese Patent Publication No. 52-4878). This diagnosis apparatus uses an indifferent electrode firmly attached to a part of the body and a plurality of different electrodes attached to the "Seiketsu" point at the symmetrical locations of the extremities, at the fingertips of both hands, for example. A d-c voltage of 2-3V is applied across the different and indifferent electrodes to measure the settled values of d-c resistance or d-c current on the skin surface measured separately at the "Seiketsu" points at the fingertips of right and left hands. Based on the measurement results, the functional condition of the internal organs and the autonomic nervous system is checked.

This apparatus for diagnosing the functional condition of the internal organ and the autonomic nervous system, however, involves measurement of only the settled values of d-c resistance or d-c current, which give less information on the living body.

DISCLOSURE OF INVENTION

After continued research efforts on the apparatus for diagnosing the functions of the internal organs and the autonomic nervous system of the abovementioned type, the present inventor and others have discovered that various types of information on the living body can be obtained by applying a constant voltage across two electrodes attached to the living body to measure not only the settled values of electric current flowing across the electrodes but also the current values that change continuously from the instant at which the constant voltage is applied.

In order to obtain information on the living body, it is desirable to diagnose the functional condition of multiple internal organs and the balance condition of the autonomic nervous system governing each organ in a short perior of time by collecting numerous data dynamically and at high speed by means of electrodes attached to multiple particular minute locations of the living body.

Consequently, the apparatus for diagnosing the functional condition of the internal organs and the autonomic nervous system of this invention is characterized in having a group of two or more electrodes attached to the living body, an electrode scanning means for scanning the group of electrodes, a constant voltage generating means for generating a constant voltage to be applied across the electrodes, a detecting means for detecting a current that flows across the electrodes and changes from time to time, and a recording means for recording the data on the instantaneous current values detected by the detecting means as the information on the living body.

The apparatus of this invention also has a calculating means for calculating various parameters based on the data on the instantaneous current values recorded by the recording means to obtain much more pieces of information on the living body. Furthermore, this invention makes it possible to easily diagnose the functional condition of each internal organ and the balance condition of the autonomic nervous system by visually representing on a display means the information on the living body obtained by the recording means and the calculating means.

BEST MODE FOR CARRYING OUT THE INVENTION

Figure 1:
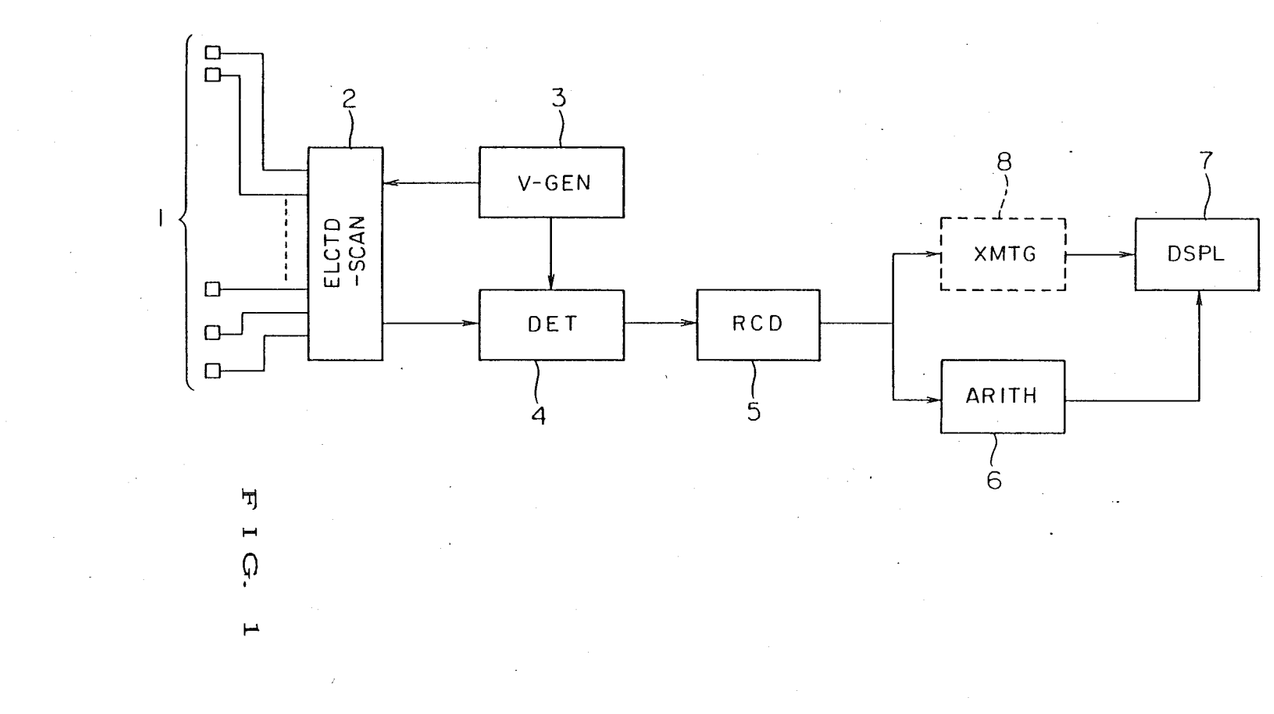
FIG. 1 is a block diagram illustrating the basic configuration of the apparatus for diagnosing the functions of the internal organs and the autonomic nervous system of this invention.

FIG. 1 is a block diagram illustrating the basic configuration of the apparatus for diagnosing the functions of the internal organs and the autonomic nervous system of this invention. The apparatus for diagnosing the functions of the internal organs and the autonomic nervous system of this invention basically has an electrode scanning means (ELCTD-SCAN) 2 to which two or more electrodes 1 attachable to the living body are connected, a constant voltage generating means (V-GEN) 3 for generating a constant voltage across the electrodes 1, a detecting means (DET) 4 for detecting dynamically and at high speed the instantaneous value of a current which flows across the electrodes during voltage application, and a recording means (RCD) 5 for recording the instantaneous current value detected.

According to an embodiment of this invention, a calculating means (ARITH) 6 for calculating a predetermined set of parameters based on the instantaneous current value recorded by the recording means 5, a display means (DSPL) 7 using an appropriate display unit, such as a cathode ray tube (CRT) or a light-emitting diode (LED) array, which is capable of visually representing the calculated parameters are provided. According to another embodiment of this invention, the data recorded by the recording means 5 may be directly displayed on the display means 7 by connecting the recording means 5 to the display means 7 by a transmitting means (XMTG) 8, instead of providing the calculating means 6. Furthermore, all the calculating means 6, the displaying means 7 and the transmitting means 8 may be provided.

The calculating means 6 calculates at least any one of the five parameters; (1) the peak value, (2) the settled value, (3) the fluctuation time, (4) the integrated surface area value during fluctuation time, (5) the slope of tangent at a given moment during fluctuation time; of a current flowing across any one pair of two electrodes among a plurality of the electrodes 1 attached to the living body when a constant voltage is applied across the two electrodes.

Figure 2:
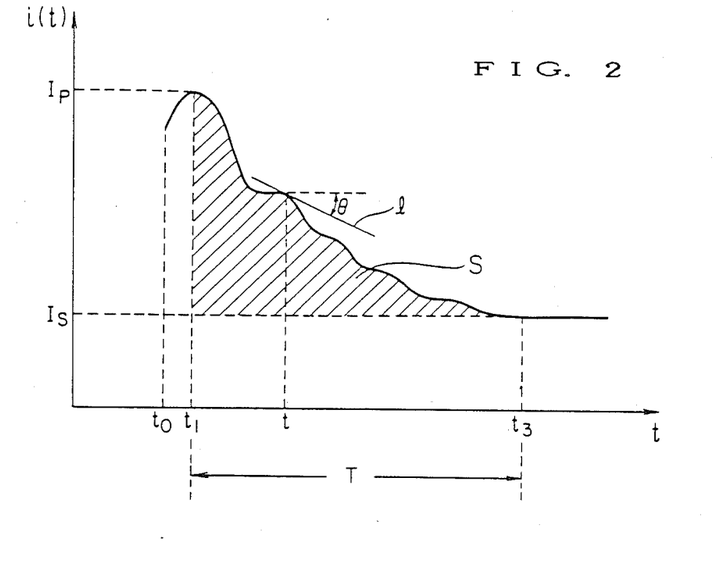
FIG. 2 is a waveform diagram of a current flowing across two electrodes.

FIG. 2 shows the waveform of a current i flowing across two electrodes when a constant voltage of a half-cycle rectangular wave is applied across the two electrodes at a time $t_0$. The current reaches the peak thereof at time $t_1$, gradually attenuates while fluctuating, and settles to a certain value at time $t_3$. In this current waveform, the current value $I_p$ at time $t_1$ is a peak value, and the current value $I_S$ at time $t_3$ is a settled value. Fluctuation time means the time T elapsed from the time $t_1$ at which the peak value is reached to the time $t_3$ at which settling begins. The integrated surface area during fluctuation time can be expressed by the following equation;

$$S = \int_{t_1}^{t_3} i(t)dt - I_S \times T$$

where the current waveform, that is, the surface area S during the period elapsed from time $t_1$ to time $t_3$, as shown by a hatched portion in FIG. 2, is the function of time, i(t). The slope of tangent at a given time during fluctuation time is the slope of tangent l of the current waveform at a given time t in the current waveform shown in FIG. 2, $$\tan\theta = \frac{d}{dt} i(t)$$

Various measurements made by the present inventor and others confirm that the peak value $I_p$ is related to one of the functions of the "Keiraku" system, the degree of activation of the living body, for example, the settled value $I_S$ to the condition of the autonomic nervous system of the living body, for example, the fluctuation time T to the electrophysiological response time (depolarization time), for example, the integrated surface area during fluctuation time to the homeostatic function of the living body (such as the functions of the immunity system, and the allergic constitution), and the slope of tangent tan $\theta$ to the speed of the defense reaction of the body, such as rheumatic symptoms, for example, respectively.

Figure 3:
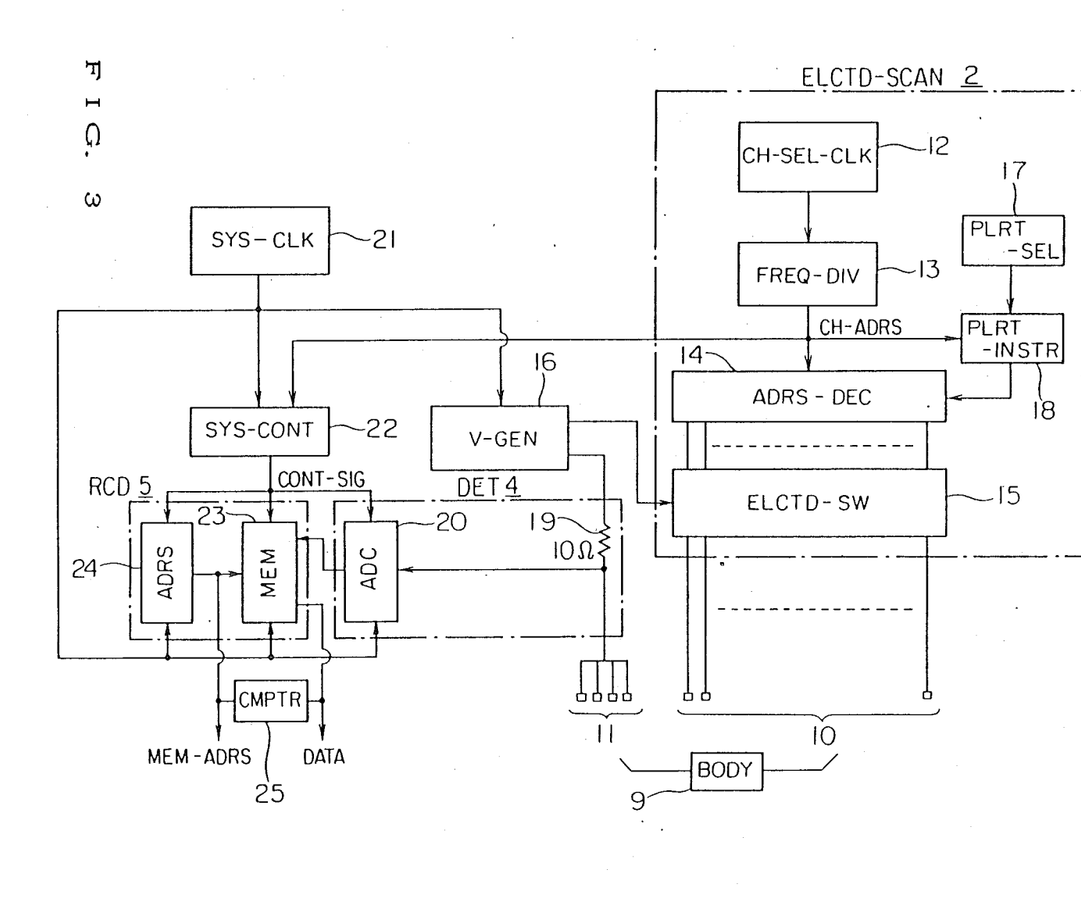
FIG. 3 is a block diagram illustrating the circuit configuration of a part of the apparatus for diagnosing the functions of the internal organs and the autonomic nervous system shown in FIG. 1.

Next, an example of the circuit configuration of the apparatus for diagnosing the functions of the internal organs and the autonomic nervous system shown in FIG. 1, consisting of the electrode scanning means 2, the constant voltage generating means 3, the detecting means 4 and the calculating means 6, will be described, referring to FIG. 3. In the circuit configuration shown, there are 24 different electrodes 10, comprising 24 channels, and four indifferent electrodes 11. These different electrodes 10 and indifferent electrodes 11 are attached to the living body 9.

The electrode scanning means (ELCTD-SCAN) 2 has a channel select clock circuit (CH-SEL-CLK) 12 for sequentially switching the 24 channels of the different electrodes 10, and generating a clock for determining the scanning speed thereof. The clock generated by the channel select clock circuit 12 is frequency-divided by a frequency divider (FREQ-DIV) 13, waveform-shaped so that a duty ratio of 1:1 is reached, converted from a serial to a parallel form, and fed to an address decoder (ADRS-DEC) 14 as a channel address (CH-ADRS). The address decoder 14 decodes the address to sequentially output a selected signal to the output terminals of the 24 channels.

Furthermore, the electrode scanning means 2 has a polarity select section (PLRT-SEL) 17 having a manual switch. An instruction from this polarity select section 17 is fed to a polarity select instruction generating section (PLRT-INSTR) 18, where a polarity select instruction is generated by means of the channel address fed from the frequency divider 13 and fed to the address decoder 14. The address decoder 14 incorporates polarity select information into a selection signal based on the polarity select instruction. The selection signal is fed to an electrode switching section (ELCTD-SW) 15 to scan sequentially or arbitrarily the 24 channels of the different electrodes 10 connected to the switching section 15 via lead wires. Thus, a voltage from a constant voltage generating circuit (V-GEN) 16 is applied sequentially or arbitrarily to the different electrodes 10. In this case, a positive half-cycle voltage of a rectangular waveform, or a negative half-cycle voltage of a rectangular waveform, or an alternating polarity 1-cycle voltage can be fed to the different electrodes 10 through selecting operation by the polarity select section 17.

The indifferent electrodes 11 are connected to the constant voltage generating circuit 16 via a resistor 19 having a resistance value of 10 ohms, for example. A current that changes from time to time flows across the scanned different electrode 10 and the indifferent electrode 11 via the living body 9, and is converted into a voltage in the resistor 19. The resistance value of the resistor 19 is desirable to be set at as small a value as possible so as to maintain a good S/N ratio.

The voltage obtained after conversion in the resistor 19 is fed to an A/D converter (ADC) 20. The start of the A/D converter 20 is controlled by a system controller (SYSCONT) 22, which generates a control signal (CONT-SIG) by combining a clock from a system clock circuit (SYS-CLK) 21, which generates a clock for controlling the entire system, with a channel address from the frequency divider 13. When the A/D converter 20 starts A/D conversion, the analog voltage value from the resistor 19 is converted into a digital value and fed to a memory (MEM) 23. The resistor 13 and the A/D converter 20 comprise the detecting means (DET) 4 shown in FIG. 1.

Simultaneously with the start of the A/D converter 20, the system controller 22 feeds a control signal to the memory 23 and an address circuit (ADRS) 24, which addresses the memory 23, so as to time storage of the digital value in the memory 23. In this way, when one different electrode 10 is scanned and a constant voltage is applied to the electrode, the continuously changing current is stored in the memory 23 as a digital value. Both the memory 23 and the address circuit 24 comprise the recording means (RCD) 5 shown in FIG. 1.

Every time each different electrode 10 in the 24 channels is scanned, a digital value is stored in the memory 23, as described above. Upon completion of measurements for all the channels, all necessary data are collected in the memory 23. The data are fed to a computer (CMPTR) 25, for example, which corresponds to the calculating means 6 shown in FIG. 1. In the computer 25, at least one of the aforementioned five parameters, such as (1) the peak value $I_p$, (2) the settled value $I_S$, (3) the fluctuation time T, (4) the integrated surface area value S during fluctuation time, and (5) the slope of tangent tan $\theta$ at a give time during fluctuation time, are calculated. In this case, the timing of readout for the memory 23 and the address circuit 24 is controlled by a control signal from the system controller 22, and the data (DATA) fed from the memory 23 and a memory address (MEM-ADRS) from the address circuit 24 are fed to the computer 25 simultaneously.

Figure 4:
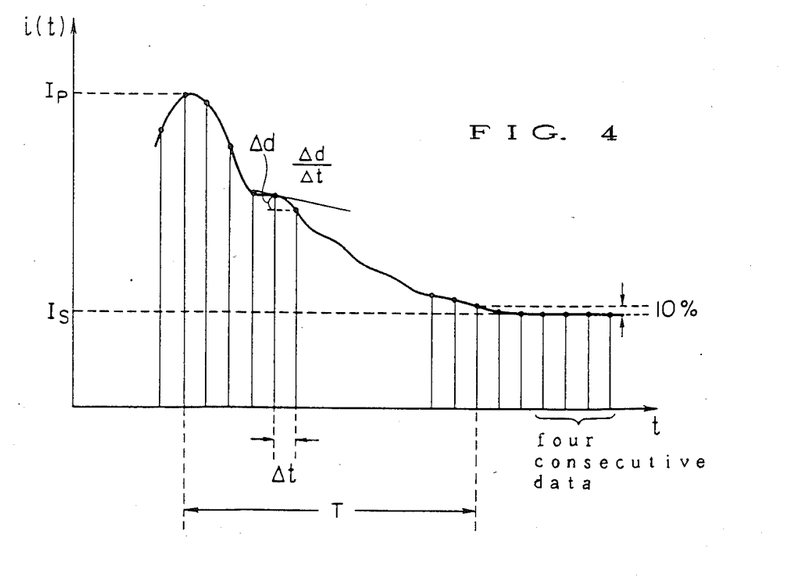
FIG. 4 is a diagram of assistance in explaining the concept of calculating the information on the living body by a computer.

Next, the concept of calculation of the aforementioned five parameters in the computer 25 will be described. FIG. 4 shows the waveform of a current flowing across the different and indifferent electrodes when a constant voltage is applied to the scanned different electrode 10 (similar to the current waveform shown in FIG. 2). This current is sampled at time intervals of $\Delta t$ (sec), and each sampled value (data) is stored in the corresponding address thereof in the memory 23. As described above, the data from the memory 23 and a memory address from the address circuit 24 are fed to the computer 25. The peak value $I_p$ can be obtained by calculating the maximum value of the data stored in each memory address. The settled value $I_S$, on the other hand, can be obtained by calculating the average value of the data stored in the final consecutive addresses, for example, four memory addresses. The fluctuation time T can be obtained by retroactively obtaining memory addresses in which the data containing values within ±10% of the settled value $I_S$ obtained in the abovementioned manner are stored, subtracting the memory address storing the maximum value $I_p$ from the memory addresses thus obtained, and multiplying the resulting difference by the sampling frequency Δt. The integrated surface area value S during fluctuation time can be obtained by subtracting a value obtained by multiplying the number of addresses during fluctuation time T by the settled value from a value obtained by summing up the data in each memory address during fluctuation time T. The slope of tangent for a current waveform at a given time during fluctuation time T can be obtained by calculating the difference Δd between the data in a memory address storing the data at a given time and the data stored in the address next to the abovementioned memory address, and dividing the difference by the sampling frequency Δt.

Figure 5:
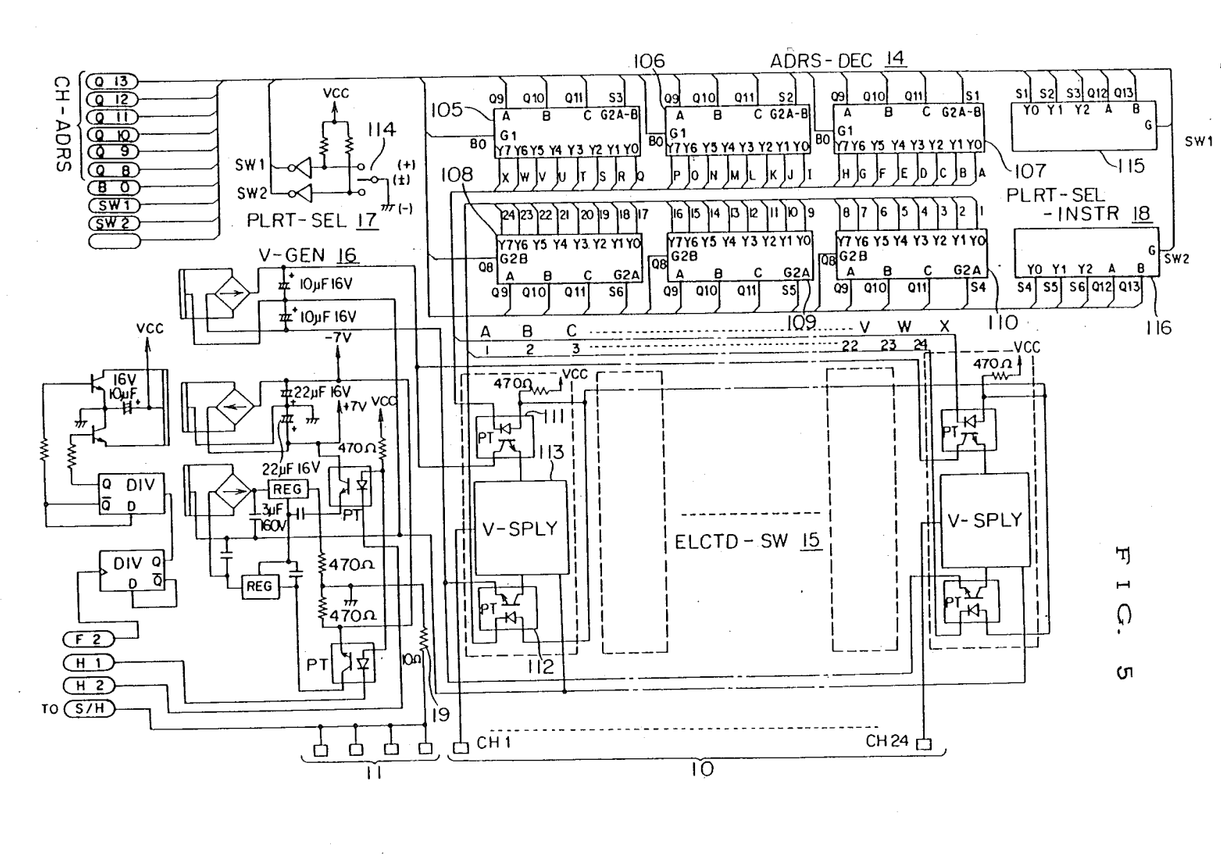
FIGS. 5 and 6 are circuit diagrams illustrating an example of the circuit configuration shown in FIG. 3.
Figure 6:
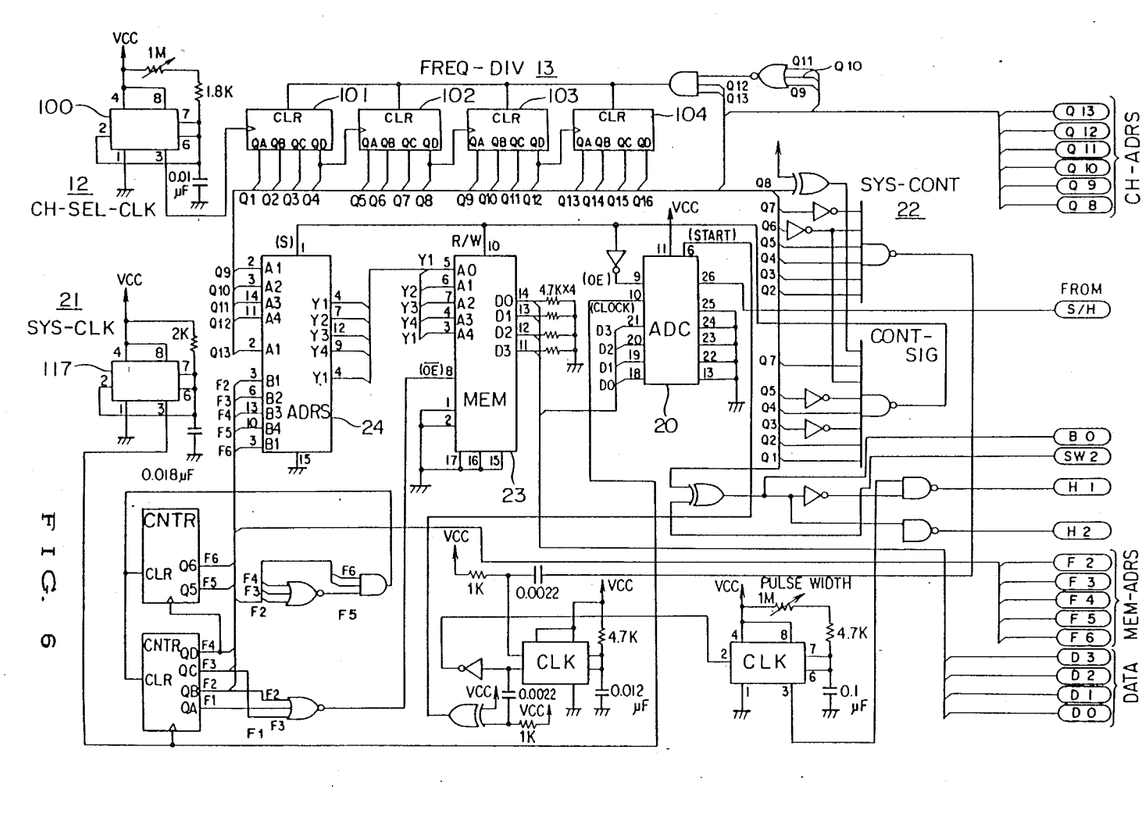

Next, a specific example of the circuit configuration shown in FIG. 3 will be described briefly. FIG. 5 shows a specific example of the electrode switching section 15, the address decoder 14, the polarity select section 17, the polarity select instruction generating section 18, and the constant voltage generating circuit 16 shown in FIG. 3. FIG. 6 shows a specific example of the channel select clock circuit 12, the frequency divider 13, the A/D converter 20, the system clock circuit 21, the system controller 22, the memory 23, and the address circuit 24 shown in FIG. 3.

In FIG. 6, a clock generated by a clock generating circuit 100 of the channel select clock circuit (CH-SEL-CLK) 12 is frequency-divided by the frequency divider (FREQ-DIV) 13 having four frequency dividing circuits 101, 102, 103 and 104, subjected to serial/parallel conversion, and outputted to terminals Q8, Q9, Q10, Q11 and Q12 as a channel address (CH-ADRS). The channel address is fed to the address decoder (ADRS-DEC) 14 having IC circuits 105, 106, 107, 108, 109 and 110 shown in FIG. 5. The address decoder decodes addresses to output sequential selection signals to output terminal for the 24 channels. The selection signals are inputted to the electrode switching section (ELCTD-SW) 15 for switching the different electrodes 10.

The electrode switching section 15 has for each channel photocouplers (PT) 111 and 112 for selecting the polarity of a voltage being supplied, and a voltage supply circuit (V-SPLY) 113 to which the different electrodes 10 are connected. The photocoupler 111 is connected to the positive side of the constant voltage generating circuit (V-SPLY) 113, and the photocoupler 112 to the negative side of the constant voltage generating circuit 16. In FIG. 5, the electrode switching section 15 is shown as having channels 1 and 24 only for the sake of clarity.

The polarity of the constant voltage to be applied to the different electrodes 10 is selected by changing over a switch 114 of the polarity select section (PLRT-SEL) 17. Changing over the switch 114 permits any of a positive half-cycle voltage, a negative half-cycle voltage, or an alternating polarity 1-cycle voltage to be applied to the different electrodes 10. An instruction from the polarity select section 17 is inputted to the polarity select instruction generating section (PLRT-SEL-INSTR) 18 having IC circuits 115 and 116. In the polarity select instruction generating section 18, a polarity select instruction is generated using a channel address inputted via terminals Q12 and Q13, and inputted to the address decoder 14. In the address decoder 14, the information on polarity selection is also incorporated in a selection signal being outputted on the basis of the polarity select instruction. When this selection signal is inputted to the electrode switching section 15, the photocouplers 111 and 112 are operated, a positive half-cycle voltage, a negative half-cycle voltage, or an alternating polarity 1-cycle voltage is fed to the different electrodes 10.

When a voltage is applied to the different electrodes 10, a current flows across the different electrode 10 and the indifferent electrode 11. The current is converted into a voltage by the resistor 19 and fed to the A/D converter 20 shown in FIG. 6 via a terminal S/H. A clock from the clock generating circuit 117 of the system clock circuit (SYS-CLK) 21, and a channel address from the frequency divider (FREQ-DIV) 13 are inputted to the system controller (SYS-CONT) 22 to produce a control signal (CNT-SIG). The control signal is inputted to the A/D converter 20, the memory (MEM) 23 and the address circuit (ADRS) 24 for the control thereof.

Simultaneously with the start of the A/D converter 20, the system controller 22 times storage of digital values in the memory 23. When one of the different electrodes 10 is scanned and a constant voltage is applied in this way, a current that changes from time to time is stored in the memory 23 as a digital value. Every time each different electrode in the 24 channels is scanned, a digital value is stored in the memory 23, as described above. Upon completion of measurements for all the channels, all necessary data are stored in the memory 23.

To read the data stored in the memory 23, the timing of readout of the memory 23 and the address circuit 24 is controlled by a control signal transmitted from the system controller 22. Data (DATA) are outputted from the memory 23 to terminals D0, D1, D2 and D3, and memory addresses (MEM-ADRS) are outputted from the address circuit 24 to terminals F2, F3, F4 and F6. The functions of internal organs and the autonomic nervous system can be diagnosed by inputting these data and memory addresses into the computer 25 (refer to FIG. 3) which calculates various parameters described above, and the calculated parameters are displayed on an appropriate display means.

Figure 7:
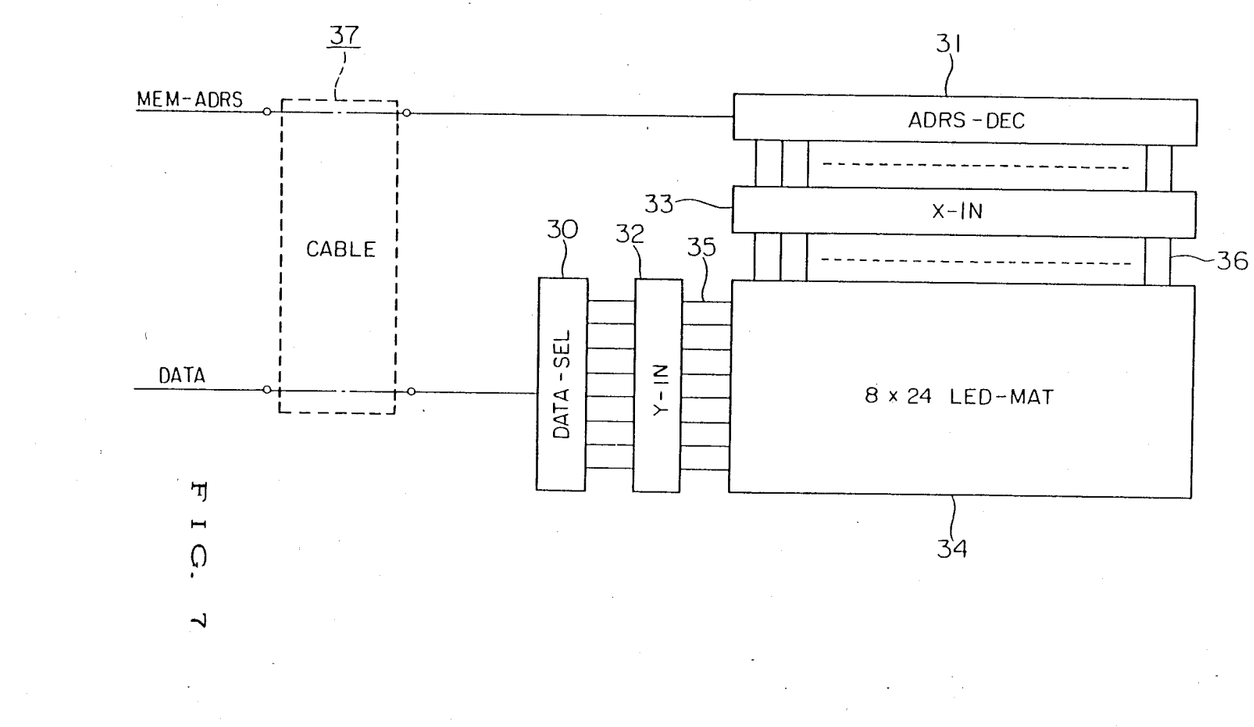
FIG. 7 is a block diagram illustrating the circuit configuration of an LED display unit.

The foregoing is concerned with the case where various pieces of information on the living body are calculated by the computer. It is possible to directly display the data stored in the memory 23 as the information on the living body, together with memory addresses, on a display means, such as a CRT or an LED display unit, via a transmitting means, such as a cable. In the following, an example where data are displayed as a bar chart on an LED display unit having light-emitting diodes arranged in an X-Y matrix will be described. FIG. 7 shows an example of the 8×24 matrix LED display unit. As data (DATA) and memory addresses (MEM-ADRS) are inputted via a cable 37, the data are fed to a data select circuit (DATA-SEL) 30, and the memory addresses are fed to an address decoder (ADRS-DEC) 31. In the data select circuit 30, 3-bit binary data, for example, are converted into 8-bit binary data and inputted to a Y-axis input circuit (Y-IN) 32. The address decoder 31, on the other hand, decodes the memory addresses to obtain signals for designating each of the 24 channels corresponding to the 24 different electrodes shown in FIG. 3. The designating signals are inputted to an X-axis input circuit (X-IN) 33. The output terminals each of the Y-axis input circuit 32 and the X-axis input circuit (X-IN) 33 are connected to the Y-axis conductors 35 and X-axis conductors 36, respectively, of the LED matrix circuit (LED-MAT) 34. The LED matrix circuit 34 has 8×24 LEDs arranged so as to intersect with the Y-axis conductors 35 and the X-axis conductors 36. Using this type of display means, data (peak values or settled values) can be displayed in a bar chart form for each channel by causing an LED train on a vertical column of the LED matrix to correspond to one channel and lighting up the LEDs upwards from the lowermost LED row in the matrix.

Figure 8:
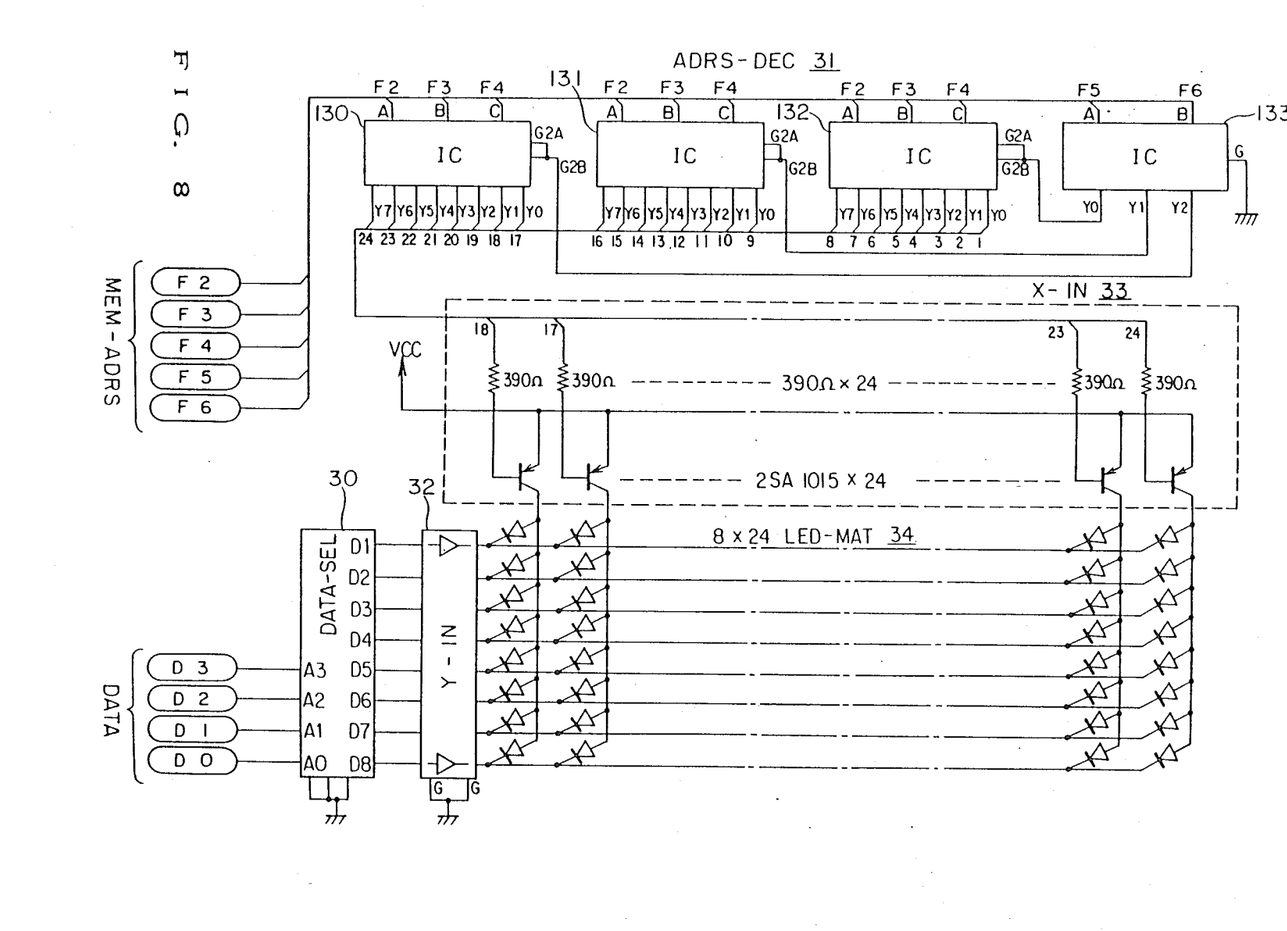
FIG. 8 is a circuit diagram illustrating an example of the circuit configuration shown in FIG. 7.

FIG. 8 shows an example of the circuit of the LED display unit shown in FIG. 7. To this LED display unit, data (DATA) and memory addresses (MEM-ADRS) are inputted from the circuit shown in FIG. 6. The memory addresses are inputted to the address decoder (ADRS-DEC) 31 having IC circuits 130, 131, 132 and 133. The output of the address decoder 31 is inputted to the X-axis input circuit (X-IN) 33 consisting of 24 resistors and 24 transistors. The data, on the other hand, are inputted to the data select circuit (DATA-SEL) 30 and converted into 8-bit binary data, and then inputted to the Y-axis input circuit (Y-IN) 32. The LED matrix circuit (LED-MAT) 34 consisting of an LED array arranged in an 8×24 matrix is capable of displaying a bar chart upon receipt of input signals from the X-axis input circuit 33 and the Y-axis input circuit 32.

Figure 9:
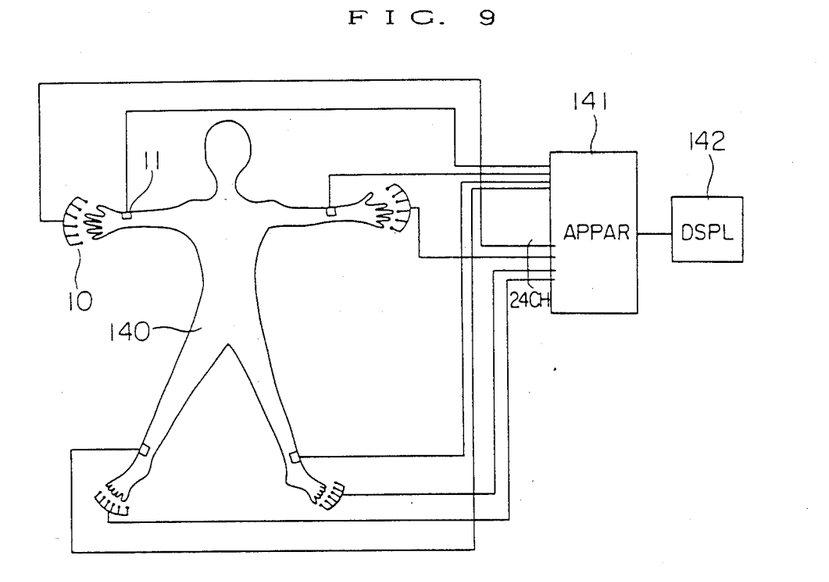
FIG. 9 is a diagram of assistance in explaining the mode of use of the apparatus for diagnosing the functions of the internal organs and the autonomic nervous system of this invention.
Figure 10:
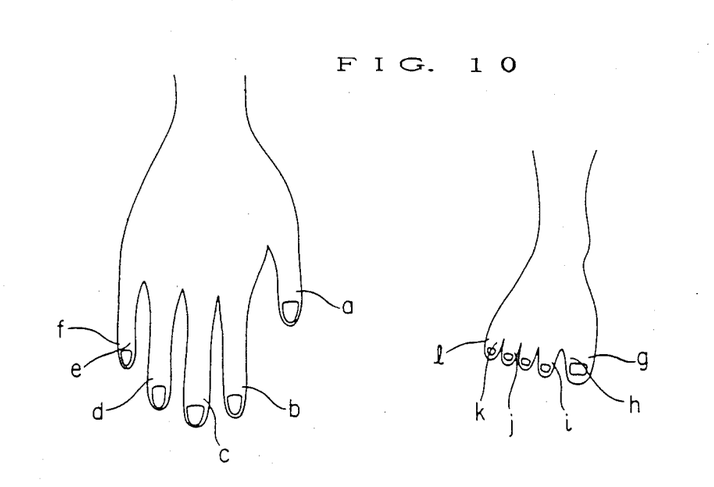
FIG. 10 is a diagram illustrating the locations of the terminal points, "Seiketsu" points, on the tips of fingers and toes.

In the following, description will be made on the mode of use of the apparatus for diagnosing the functions of the internal organs and the autonomic nervous system in conjunction with the aforementioned LED matrix display unit which displays the information on the living body in a bar chart form. FIG. 9 shows the state where 24 pieces of the different electrodes 10 and 4 pieces of the indifferent electrodes 11 are attached to the living body 140. The indifferent electrodes 11 are attached to the wrists of both hands and the ankles of both feet of the living body, while the different electrodes 10 are attached to the "Seiketsu" points, which are the "Keiketsu" terminal points at the tips of both fingers and toes. In FIG. 10, symbols a - l indicate the locations of the "Seiketsu" points to which the different electrodes are attached. In the figure, only the right hand and the right foot are shown, but the different electrodes are also attached to the "Seiketsu" points on the left hand and the left foot at symmetrical locations to the "Seiketsu" points on the right hand and the right foot. Each of these "Seiketsu" points has the particular name thereof which is related to each internal organ related to each "Keiraku" system. These names are listed below.

a: Hai-kei (system pertaining to the lung)
b: Daicho-kei (system pertaining to the large intestine)
c: Sinho-kei (system pertaining to the heart constrictor)
d: Sansho-kei (system pertaining to the heart)
e: Sin-kei (system pertaining to the heart)
f: Shocho-kei (system pertaining to the small intestine)
g: Hi-kei (system pertaining to the spleen)
h: Kan-kei (system pertaining to the liver)
i: I-kei (system pertaining to the stomach)
j: Tan-kei (system pertaining to the gallbladder)
k: Jin-kei (system pertaining to the kidney)
l: Boko-kei (system pertaining to the urinary bladder)

Figure 11:
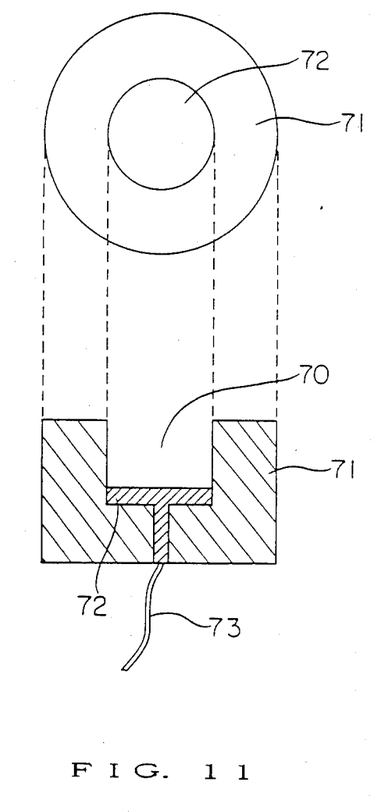
FIG. 11 is a diagram illustrating an example of electrode.

FIG. 11 shows the plan and cross-sectional views of an example of the electrode to be attached to a "Seiketsu" point at any of the abovementioned locations. This electrode has a cylindrical insulating member 71 having a recess 70. On the bottom of the recess 70 provided is an electrode 72 having a diameter of 1-10 mm. The depth of the recess 70 down to the electrode 72 is 1-10 mm. A lead wire 73 is connected to the electrode 72. The different electrode of this construction is forced onto a "Seiketsu" point at which information on the living body is to be obtained, by applying electrically conductive cream to the recess 70.

Figure 12:
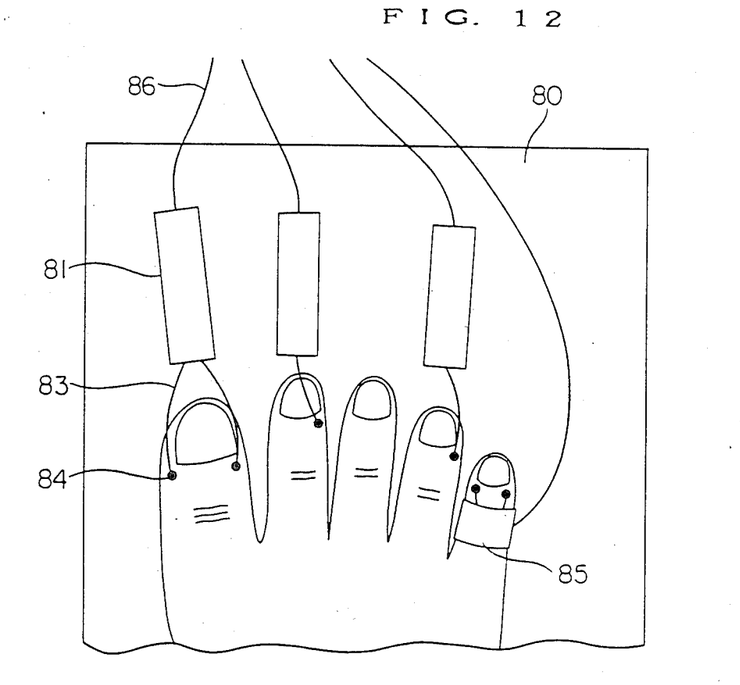
FIG. 12 is a diagram illustrating another example of electrode.
Figure 13:
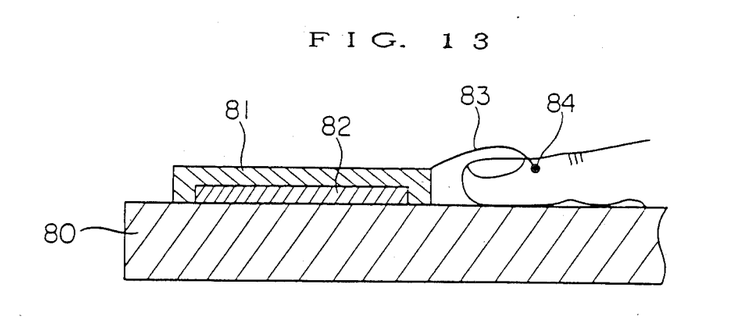
FIG. 13 is a cross sectional view of the electrode shown in FIG. 12.

FIGS. 12 and 13 are the plan and cross-sectional views, respectively, of another example of the different electrode suitable for measuring the "Seiketsu" points on the toetips. A magnet 82 is embedded in an electrode support 81, and an elastic conductor is attached to the electrode support 81 in such a manner as to protrude therefrom. At the end of the elastic conductor provided is an electrode 84. To an electrode support 85 of a ring type for use with the little toe, also attached is an elastic conductor having an electrode at the end thereof. Each elastic conductor is connected to a lead wire 86. When using different electrodes of this type, the foot of a subject is placed on a magnetic material plate 80, with the electrode supports 81 disposed so that the electrodes 84 come in contact with the "Seiketsu" points on the toes. The electrode support 81 can be securely attached onto the magnetic material plate 80 by the attractive force of the magnet embedded in the electrode support 81. The electrode 4 is forced onto the "Seiketsu" point of the toe by the resiliency of the eleastic conductor 83. The electrode support 85 of a ring type is used for the little toe because the electrode support 81 cannot be attached precisely to the "Seiketsu" point due to the small size of the little toe.

In the foregoing, examples of the different electrode 10 have been described. For the indifferent electrodes 11, plate-shaped electrodes having a wide contact surface area may be used so as to permit the electrodes to be easily attached to the wrists and the ankles. As described above, the indifferent electrodes 11 are attached to the wrists of both hands and the ankles of both feet. The reason why the indifferent electrodes are attached symmetrically to the left and right parts of the living body is to balance electrical resistances between the different electrodes and the indifferent electrodes to eliminate measurement errors due to the difference in the attaching locations of the indifferent electrodes.

Now, return to FIG. 9. After the different and indifferent electrodes are attached to the living body, as described above, the apparatus for diagnosing the functions of the internal organs and the autonomic nervous system (APPAR) 141 sequentially scans each of the different electrodes 10, applies a positive half-cycle voltage, for example, to each different electrode, and measures currents flowing across the different electrodes and the indifferent electrodes. The measured currents are stored in the form of digital values in the memory of the apparatus (APPAR) 141. The data read from the memory is displayed directly on the LED display unit (DISPL) 142.

Figure 14:
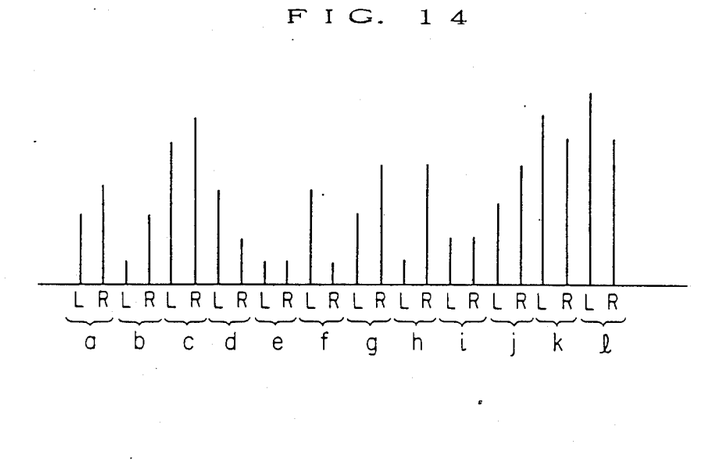
FIG. 14 is a diagram illustrating an example of barchart representation on the display unit.

FIG. 14 shows an example of a bar chart displayed on the LED display unit 142. In the figure, symbols a to f denote the information on the living body at the "Seiketsu" points on the fingers shown in FIG. 10, and symbols g to l the information on the living body at the "Seiketsu" points on the toes. L denotes the left fingers and toes, and R the right fingers and toes. The length of each bar indicates the peak value or the settled value. By the use of this bar chart, the functions of the internal organs and the autonomic nervous system can be diagnosed.

Figure 15:
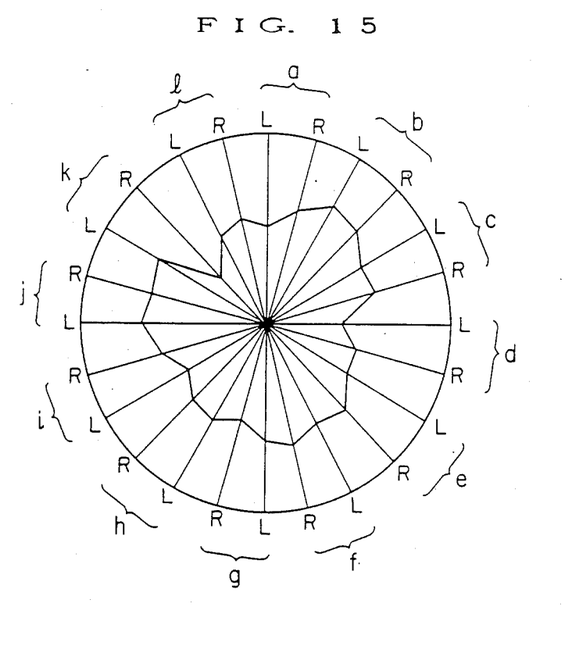
FIG. 15 is a diagram illustrating an example of radar chart representation on the display unit.

Although the foregoing is an example where the information on the living body is displayed in the form of a bar chart on the LED display unit, the information on the living body can be displayed in the form of a radar chart by changing the arrangement of LEDs on the LED display unit. FIG. 15 shows an example of the radar chart.

Although the data read from the memory is displayed on the display means in the foregoing examples, the information on the living body calculated by the computer may also be displayed. In such a case, too, the information on the living body at each "Seiketsu" point can be displayed in a bar chart or radar chart.

Furthermore, 24 pieces of different electrodes are attached to "Seiketsu" points and scanned by an electrode scanning means in the foregoing examples. A single different electrode, however, may be used to measure the information on the living body at each "Seiketsu" point by sequentially forcing the electrode onto the "Seiketsu" points being measured. In this case, no electrode switching operation is carried out in the electrode switching section of the apparatus of this invention. In the foregoing examples, the voltage to be applied to the different electrodes is of a rectangular waveform. The voltage, however, is not limited to a rectangular waveform, but may be of any other waveform.

INDUSTRIAL APPLICABILITY

As described in detail in the foregoing, the apparatus for diagnosing the functions of the internal organs and the autonomic nervous system of this invention makes it possible to measure at high speed a current that changes from time to time at each "Keiketsu" point. Consequently, various types of information on the living body can be obtained by analyzing the current or calculating various parameters, such as the peak value, the settled value, the fluctuation time, the integrated surface area value during fluctuation time, the slope of tangent at a given time during fluctuation time. Based on the information on the living body thus obtained, it is made possible to easily diagnose the functional condition of the internal organs and the autonomic nervous system.

The apparatus for diagnosing the functions of the internal organs and the autonomic nervous system of this invention can be utilized not only for detecting information on the living body but also for analyzing the depolarization characteristics of an eletrolytic solution.

Furthermore, the apparatus of this invention, which is capable of translating the amount of chemical reaction into a physical quantity, can be used for qualitative analysis of chemical substances and solutions. In addition, the apparatus of this invention is expected to be used for quantitative analysis of chemical substances and solutions in the future.

I claim:

1. An apparatus for diagnosing the functions of the internal organs and the autonomic nervous system of the living body which diagnoses the functional condition of the internal organs and the balance condition of the autonomic nervous system of the living body by applying a voltage to particular minute portions of the living body and measuring current flowing in the particular minute portions, and characterized in that an electrode group consisting of two or more electrodes (1) securely attachable to the living body,
an electrode scanning means (2) for scanning said electrode groups,
a constant voltage generating means (3) for generating a constant voltage to be applied across said electrodes via said electrode scanning means,
a detecting means (4) for detecting at high speed a current i (t) that flows across said electrode pairs and changes from time to time, and
a recording means (5) for recording as the information on the living body the data on the instantaneous values of the current detected by said detecting means are provided, calculating means (6) for calculating at least one parameter as the information on the living body from the data on the instantaneous values of the current recorded in said recording means is provided,
said at least one parameter being any of:
  (1) the peak value $1_p$,
  (2) the settled value $I_S$
  (3) the fluctuation time $T = t_s - t_p$ elapsed from the time $T_p$ at which the peak value is reached to the time $t_s$ at which the settled value is reached,
  (4) the integrated surface area values during fluctuation time $$S = \int_{t_p}^{t_s} i(t)dt - I_s \times T$$

(5) the slope of tangent at a given time with respect to the current waveform $$\tan\theta = \frac{d}{dt} i(t)$$

of the wave form of a current i (t) that changes from time to time.

2. An apparatus for diagnosing the functions of the internal organs and the autonomic nervous system of the living body as claimed in claim 1 wherein a display means (7) for displaying the information on the living body calculated by said calculating means (6) is provided.

3. An apparatus for diagnosing the functions of the internal organs and the autonomic nervous system of the living body as claimed in claim 2 characterized in that said apparatus measures a current flowing in a "Keiketsu" point as a particular minute portion of the living body.

4. An apparatus for diagnosing the functions of the internal organs and the autonomic nervous system of the living body as claimed in claim 2 wherein a transmitting means (8) for transmitting the information on the living body recorded in said recording means to said display means is provided.

5. An apparatus for diagnosing the functions of the internal organs and the autonomic nervous system of the living body as claimed in claim 4 characterized in that said apparatus measures a current flowing in a "Keiketsu" point as a particular minute portion of the living body.

6. An apparatus for diagnosing the functions of the internal organs and the autonomic nervous system of the living body as claimed in claim 1 characterized in that said apparatus measures a current flowing in a "Keiketsu" point as a particular minute portion of the living body.

7. An apparatus for diagnosing the functions of the internal organs and the autonomic nervous system of the living body as claimed in claim 6 wherein said electrode group consists of one or more different electrodes (10) securely attachable to the "Keiketsu" points of the living body and one or more indifferent electrodes (11) securely attachable to parts of the living body.

8. An apparatus for diagnosing the functions of the internal organs and the autonomic nervous system of the living body as claimed in claim 7 wherein said electrode scanning means (2) scans said different electrodes.

9. An apparatus for diagnosing the functions of the internal organs and the autonomic nervous system of the living body as claimed in claim 8 wherein a constant voltage generated by said constant voltage generating means (3) is applied across a scanned different electrode and said indifferent electrode.

10. An apparatus for diagnosing the functions of the internal organs and the autonomic nervous system of the living body as claimed in claim 9 wherein said display means (7) displays the information on the living body at each "Keiketsu" point.

* * * * *